US005672732A

United States Patent [19]

Agterberg et al.

[11] Patent Number: 5,672,732
[45] Date of Patent: Sep. 30, 1997

[54] PROCESS FOR THE CARBONYLATION OF BUTADIENE OR A BUTADIENE DERIVATIVE

[76] Inventors: Frank P. W. Agterberg, Gelders Overkwartier 9, 6118 EH Susteren; Otto E. Sielcken, van Gelre Gulikstraat 61, 6137 HB Sittard, both of Netherlands; Michael B. D'Amore, 2406 Granby Rd., Wilmington, Del. 19810; Harold S. Bruner, 10 Forest Creek Dr., Hockessin, Del. 19707

[21] Appl. No.: 605,590

[22] Filed: Feb. 22, 1996

Related U.S. Application Data

[63] Continuation-in-part of Ser. No. 393,313, Feb. 22, 1995.
[51] Int. Cl.[6] ............................................. C07C 67/36
[52] U.S. Cl. ................................... 560/207; 562/522
[58] Field of Search .............................. 562/522; 560/207

[56] References Cited

U.S. PATENT DOCUMENTS

| | | | |
|---|---|---|---|
| 4,124,617 | 11/1978 | Knifton | 562/522 |
| 4,172,087 | 10/1979 | Knifton | 562/522 |
| 4,739,109 | 4/1988 | Drent | 560/207 |
| 4,739,110 | 4/1988 | Drent | 562/522 |
| 4,902,822 | 2/1990 | Drent | 562/522 |
| 5,026,901 | 6/1991 | D'Amore | 560/207 |
| 5,028,576 | 7/1991 | Drent | 560/207 |
| 5,028,734 | 7/1991 | Drent | 562/522 |
| 5,103,043 | 4/1992 | Drent | 560/207 |
| 5,149,868 | 9/1992 | Drent | 562/522 |
| 5,292,944 | 3/1994 | Asadan | 562/522 |

FOREIGN PATENT DOCUMENTS

| | | |
|---|---|---|
| 190473 | 8/1986 | European Pat. Off. . |
| 271145 | 6/1988 | European Pat. Off. . |

*Primary Examiner*—Paul J. Killos
*Attorney, Agent, or Firm*—Cushman Darby & Cushman IP Group of Pillsbury Madison & Sutro, LLP

[57] ABSTRACT

A process for the carbonylation of butadiene or a butadiene derivative in the presence of (i) carbon monoxide, (ii) an alcohol or water, and (iii) a catalyst system comprising palladium, a carboxylic acid and a monodentate phosphine ligand. The amounts of reactants during the carbonylation process are controlled so that the molar ratio of butadiene or butadiene derivative to palladium in the reaction mixture is less than about 70:1, the molar ratio of carboxylic acid to palladium is greater than about 10:1 and the molar ratio of alcohol or water to butadiene or butadiene derivative is less than about 2:1.2. Good selectivity and conversions are advantageously achieved.

16 Claims, No Drawings

PROCESS FOR THE CARBONYLATION OF BUTADIENE OR A BUTADIENE DERIVATIVE

CROSS-REFERENCE TO RELATED APPLICATION

This is a continuation-in-part of copending application Ser. No. 393,313 filed Feb. 22, 1995.

BACKGROUND OF THE INVENTION

1. Field of the Invention

The invention relates to a process for the carbonylation of butadiene or a butadiene derivative in the presence of (i) carbon monoxide, (ii) an alcohol or water, and (iii) a catalyst system comprising palladium, a carboxylic acid and a monodentate phosphine ligand, under controlled conditions to yield good selectivity of pentenoate product.

2. Description of Related Art

U.S. Pat. No. 5,028,734 describes in a Comparative Example 7 a batch-wise carbonylation of butadiene in the presence of ethanol and a catalyst system comprising palladium, triphenyl phosphine and 2,4,6-trimethylbenzoic acid. The molar ratio of butadiene to palladium was about 90:1 at the start of the carbonylation. The molar ratio of acid to palladium was 7.5:1, and the molar ratio of alcohol and butadiene was 2.7:1. A disadvantage of this process is that the selectivity for pentenoate ester is low: only about 75%. In addition, the conversion was only about 55%. Most of the by-products were nonadienoates.

SUMMARY OF THE INVENTION

One object for the present invention is to provide a process for the carbonylation of butadiene or a butadiene derivative wherein the selectivity and conversion to pentenoate ester or acid is higher than can be obtained with the process described in U.S. Pat. No. 5,028,734.

This and other objects are achieved in a process for the preparation of a pentenoic acid or a pentenoate ester comprising:

carbonylating butadiene or a butadiene derivative in a reaction mixture in the presence of (i) carbon monoxide, (ii) an alcohol or water, and (iii) a catalyst system comprising palladium, a carboxylic acid, and a monodentate phosphine ligand, wherein the carbonylating step is carried out either continuously, semicontinuously, or batch-wise, and the molar ratio of the butadiene, butadiene derivative, or mixture thereof to the palladium in the reaction mixture is less than about 70:1, the molar ratio of the carboxylic acid to the palladium in the reaction mixture is greater than about 10:1, and the molar ratio of the alcohol or water to the butadiene, butadiene derivative, or mixture thereof in the reaction mixture is less than about 2:1. The molar ratios are substantially maintained throughout the carbonylation.

When the process is performed in this manner, the selectivity to pentenoate ester or acid is considerably improved. An additional advantage is that the catalyst system is stable for a longer period of time and may be reused several times without loss of catalytic activity when performing the process according to the invention. A further advantage is that no halogen containing compounds and/or organic nitrogen containing base is needed to achieve favorable selectivities. In contrast, for example, the process of U.S. Pat. No. 4,172,087 requires use of an amine base.

In the aforementioned U.S. Pat. No. 5,028,734, a multidentate phosphine ligand such as 1,4-bis (diphenylphosphino) butane is used. As reported in U.S. Pat. No. 5,028,734, the improvement over the use of a monodentate phosphine ligand, without multidentate phosphine, was better selectivity for pentenoate ester. However, in the process of U.S. Pat. No. 5,028,734, relatively complex multidentate phosphine ligands are needed to achieve the improved selectivity. Multidentate phosphines decompose during carbonylation. An additional advantage of the process according to the present invention is that a comparable improved selectivity to pentenoate ester can be achieved without use of multidentate phosphine ligands.

DETAILED DESCRIPTION OF THE PRESENT INVENTION

A carbonylation reaction, as used herein, means any reaction between an unsaturated substrate, a hydroxy compound and carbon monoxide to yield an acid or ester. For example, if water is the hydroxy compound, carbonylation of butadiene yields the pentenoic acid as the main product. If the hydroxy compound is an alcohol, carbonylation of butadiene yields a pentenoate ester as the main product.

The pentenoate ester product is usually a mixture of 2-, 3- and 4-pentenoate esters. An additional advantage of the process according to the invention is that less 2-pentenoate ester is formed than in U.S. Pat. No. 5,028,734. This is particularly advantageous when the reaction product is used in the hydroformylation of pentenoate ester to the terminal 5-formylvalerate ester with a rhodium-based catalyst system, as described in, for example, U.S. Pat. No. 5,264,616, the complete disclosure of which is incorporated herein by reference. The 2-pentenoate ester has an adverse effect on the selectivity for 5-formylvalerate ester.

The alcohol is not strictly limited and can be, for example, a $C_1$–$C_{20}$ organic compound having one or more hydroxy groups. The organic compound can be an aliphatic, cycloaliphatic or aromatic compound. Exemplary compounds include, among others, phenol, cresol, tert-butyl catechol, cyclohexanol, and mixtures thereof. By preference, the alcohol is an aliphatic alcohol, ROH, in which the aliphatic group R is a linear or branched alkyl group. The alkyl group has preferably 1 to 6 carbon atoms. Alkanols of the formula ROH are useful herein and include methanol, ethanol, propanol, isopropanol, butanol, tert-butanol, pentanol and hexanol. Most preferably, methanol or ethanol is used. A substituted alcohol can be used such as, for instance, an ether-substituted alcohol, of which the methyl ether of ethylene glycol is exemplary. Mixtures of alcohols may be used.

The molar ratio of alcohol or water to butadiene in the process according to the invention is held or maintained less than about 2:1. Most preferably, this ratio is less than about 1.5:1. Preferably, the molar ratio of alcohol or water to butadiene is greater than about 0.5:1. More preferably, the amount of alcohol or water is at least the stoichiometric amount in relation to butadiene because then higher yields to the desired product can be achieved. The molar ratio of alcohol or water to butadiene is thus preferably about 1:1 or higher.

The monodentate phosphine ligand is preferably a compound represented by the general formula:

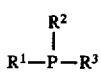

(1)

wherein $R^1$, $R^2$ and $R^3$ each individually represent an optionally substituted organic group. The organic group can be, for example, a $C_1$–$C_{20}$ alkyl group, a $C_2$–$C_{20}$ alkenyl group, a $C_6$–$C_{18}$ aryl group or a $C_4$–$C_{12}$ cyclic group in which the cyclic group also contains one or more heteroatoms such as, for example, nitrogen. Exemplary alkyl groups include, for example, methyl, ethyl, isopropyl, tert-butyl and cyclohexyl. An exemplary alkenyl group is butenyl. Exemplary cyclic groups containing heteroatoms include, for instance, 6-methyl-2-pyridyl and 4,6-dimethyl-2-pyridyl. Preferably at least one of the organic groups $R^1$, $R^2$ and $R^3$ is a $C_6$–$C_{18}$ aryl group and more preferably a $C_6$–$C_{14}$ aryl group. Exemplary aryl groups include naphthyl and phenyl. The organic group can be substituted with, for example, halogen atoms, such as, for example, Cl, Br or F, or with $C_1$–$C_6$ alkyl, $C_6$–$C_{18}$ aryl, $C_1$–$C_6$ alkoxy, carboxy, carbalkoxy, acyl, trihalogenmethyl, cyano, dialkylamino, sulfonylalkyl or alkenoyloxy groups. Substituents may be groups with electron withdrawing or electron donating properties.

Examples of monodentate phosphine ligands include tri-p-tolylphosphine, tri-p-methoxyphenylphosphine, diphenyl-pentylphosphine and dimethylphenylphosphine. Preferably, triphenylphosphine is used because this compound is generally readily available.

The molar ratio of monodentate phosphine ligand to palladium is preferably greater than about 5:1 and less than about 50:1. When this ratio is too low, the catalytic effect of the catalyst system is weaker, and by-products such as vinyl cyclohexene and high-molecular weight products may form. Multidentate phosphine ligands may, if desired, be present during the carbonylation reaction. Examples include 1,2-di(diphenylphosphino)ethane, 1,3-di(diphenylphosphino)propane, 1,4-di(diphenylphosphino)butane, 1,5-di(diphenylphosphino)pentane. Preferably, however, multidentate phosphine ligands are not used as a co-ligand because these ligands tend to decompose during reaction.

As used herein, the term butadiene derivative means compounds which yield pentenoate ester or pentenoic acid as the major product when carbonylated by the process according to the invention. Herein, all references to butadiene shall also include butadiene derivatives unless described otherwise. It is also possible to carbonylate mixtures of butadiene and butadiene derivatives. Although butadiene derivatives are readily employed, butadiene is preferred because of its availability. The butadiene can be used in pure form or in an admixture with aliphatic compounds. For instance, an exemplary admixture is the $C_4$ fraction or cut obtained in a steam cracker process. The $C_4$ fraction may, for example, comprise butadiene and 1-butene, 2-butene, and/or isomeric butynes.

Preferred butadiene derivatives are represented by the following general formulae:

(2)

(3)

wherein X is a $C_1$–$C_{20}$ organic group or an inorganic group. Examples of suitable organic groups include —$OR^4$ or —$OC(O)R^5$ groups, in which $R^4$ and $R^5$ can be, for example, a $C_1$–$C_6$ alkyl, $C_2$–$C_6$ alkenyl, a $C_6$–$C_{14}$ aryl, a $C_7$–$C_{14}$ aralkyl or a $C_7$–$C_{14}$ alkaryl group. Examples include methyl, ethyl, n-propyl, isopropyl, n-butyl, tert-butyl, pentyl, cyclopentyl, cyclohexyl, hexyl, propenyl, butenyl, pentenyl, phenyl, naphthyl, benzyl or tosyl. Examples of other suitable organic or inorganic groups include —OH, —$H_2PO_4$, —$PR^6R^7$, —NH—CO—$R^8$, —$NH_2$, and —$SR^9$, in which $R^6$, $R^7$, $R^8$ and $R^9$ can be the same as defined above for $R^4$ and $R^5$.

Specific butadiene derivatives include, for example, 1-methoxy 2-butene, 3-methoxy 1-butene, 1-ethoxy 2-butene, 3-ethoxy 1-butene, isomeric butenyl pentenoate, 1-butene 3-carbonate, 2-butene 1-carbonate, 3-hydroxy 1-butene, and 1-hydroxy 2-butene. Methods of making alkoxy butenes like methoxy butene are described in, for example, U.S. Pat. No. 4,590,300, the complete disclosure of which is incorporated herein by reference.

Any solvent, which is substantially inert under the reaction conditions, is in principle suitable as an additional solvent. Reactants or by-products may also help form the liquid phase. Exemplary reactants or by-products include pentenoate ester, $C_9$-esters and high boiling by-products. Examples of inert solvents include sulfoxides and sulfones such as dimethyl sulfoxide, diisopropyl sulfone; aromatic solvents such as benzene, toluene, xylene; esters such as methyl acetate, methyl valerate, pentenoate esters and butyrolactone; ketones such as acetone or methylisobutyl ketone; ethers such as anisole, trioxanone, diphenyl ether and diisopropyl ether; and mixtures thereof. Preferably, diphenyl ether is used as an additional solvent.

Palladium, as used herein, generally refers to one or more palladium compounds which can be present in the reaction mixture in heterogeneous or homogeneous form. However, homogeneous catalyst systems are preferred. Since palladium in situ forms a complex with the phosphine ligand, the choice of the initial Pd compound is in general not believed to be critical. Homogeneous palladium compounds include, for instance, palladium salts of nitric acid, sulfonic acid, $C_2$–$C_{12}$ alkane carboxylic acids, or the hydrogen halogenides HF, HCl, HBr, or HI. Metallic palladium can also be used. Examples of homogeneous palladium compounds include $PdCl_2$, $PdBr_2$, $PdI_2$, $Na_2PdI_4$, $K_2PdI_4$, $PdC_2$(benzonitrile)$_2$ and bis(crotylpalladium chloride). Another group of palladium compounds are halogen-free palladium complexes such as palladium acetylacetonate (Pd(acac)$_2$), palladium acetate, palladium nitrate, Pd(NO$_3$)$_2$, tetrakis(triphenyl phosphine)palladium, and di-palladium-tris(dibenzylideneacetone) Pd$_2$(dba)$_3$.

One type of suitable heterogeneous palladium compound is palladium on an ion exchanger, such as, for instance, an ion exchanger containing carboxylic acid groups. Ion exchangers containing carboxylic acid groups are commercially available under the brand names Amberlite IRC 50 and Amberlite IRC 84 (Rohm & Haas). Another possible heterogeneous catalyst is palladium complexed to immobilized phosphine on a carrier catalyst. In this case, the immobilized phosphine is the monodentate phosphine ligand of the catalyst system. Carriers include polystyrene, polyacrylamide, and silica.

The palladium concentration in the reaction mixture is preferably as high as possible because the rate of reaction per unit of reactor volume will be higher. The upper limit for a homogeneous catalyst system will normally be determined by the solubility of palladium in the reaction mixture. This will depend on the specific palladium compound used as discussed above. This upper limit can be determined by one skilled in the art.

Preferably the butadiene/palladium molar ratio is held greater than about 1:1, and more preferably, greater than about 2:1. The butadiene/palladium molar ratio is preferably held less than about 70:1, and more preferably, held less than about 50:1.

To achieve and maintain such low butadiene/palladium molar ratios, the butadiene is preferably continuously supplied to the carbonylation reaction at a rate of at most 100 mol butadiene per hour per mol palladium present during carbonylation. More preferably, this rate is less than about 80 mol butadiene per hour per mol palladium.

The carboxylic acid is preferably a $C_1$–$C_{30}$ organic compound. The pKa of the acid is preferably greater than about 2 measured in an aqueous solution at 18° C. The pKa is preferably less than about 5.0. These organic compounds may be substituted with hydroxy groups, $C_1$–$C_4$ alkoxy groups like, for example methoxy, and amine or halogenide groups like, for example Cl, I and Br. Exemplary carboxylic acids include benzoic acid, acetic acid, valeric acid, butanoic acid cyclohexylpropionic acid or nonanoic acid. It has also been found that the acid counterparts to the ester by-products of the present invention can be used. The use of these acids is advantageous because they are readily obtainable by hydrolysis of the ester by-products. Examples of these acid hydrolysis products include nonadienoic acid, pentenoic acid, 1-butene-2-carboxylic acid and methyl-substituted butenoic acid.

Preferably, the acid is a sterically hindered carboxylic acid having a pKa of less than about 4.5. Exemplary sterically hindered carboxylic acids include sterically hindered benzoic acids, including, for example, $C_1$–$C_4$ alkyl substituted benzoic acids like 2,6-dimethylbenzoic acid and 2,4,6-trimethyl benzoic acid. These also include hydroxy substituted benzoic acids like, for example, meta- and parahydroxybenzoic acid and other substituted benzoic acids like, for example, 2,6-difluorobenzoic acid or 2,4,6-tribromobenzoic acid.

The carboxylic acid is preferably pentenoic acid when the pentenoate ester is the desired end product. Under some carbonylation conditions, the carboxylic acid of the catalyst system is consumed during the reaction. The carboxylic acid may, for example, react with alcohol to form the corresponding ester. By using pentenoic acid as co-catalyst, the desired end product (the pentenoate ester) is obtained as the reaction product of the pentenoic acid. Fresh pentenoic acid needed to replace the consumed pentenoic acid can be prepared by hydrolysis of a portion of the pentenoate ester obtained in the process according to the invention. Another preferred carboxylic acid is a nine-carbon carboxylic acid which may be saturated or unsaturated. Examples of nine-carbon saturated carboxylic acid include nonanoic acid.

An example of nine-carbon unsaturated carboxylic acid is nonadienoic acid. The corresponding ester is formed as a by-product in the process according to the invention. Thus the acid can be formed by a simple hydrolysis of this ester by-product. Such hydrolysis can be performed in a separate step, for example, by contacting some of the pentenoate ester with an acid ion exchange resin in the presence of water. Alternatively, one of the distillation columns used for separating the pentenoate ester from one of the other components of the catalyst system present in the effluent of the reactor may be used for hydrolysis. This hydrolysis can be effected by contacting the pentenoate ester in the column with, for example, an acid ion exchanger in the presence of water.

The addition of small amounts of water to the carbonylation reaction to pentenoate ester will result in a stable concentration of pentenoic acid in a continuous process. The amount of water needed will depend on the amount of pentenoic acid consumed by esterification during the carbonylation. The rate of esterification will depend on the reaction conditions which are selected and can be easily determined by analyzing the reaction mixture leaving the reactor. If a carboxylic acid other than pentenoic acid is used, the esters formed can also be hydrolyzed as described above in a separate hydrolysis to the original acid. The resultant acid can be then reused in the process.

When water is used as the hydroxy group containing compound in the carbonylation reaction, pentenoic acid is the main product, and esterification of the acid co-catalyst cannot occur. Alcohol is generally not present when water is used. In such a process the pentenoic acid formed may also serve as the acid co-catalyst according to the process according to the invention. Adding a different carboxylic acid is however possible. Examples of these carboxylic acids include the same as described above.

The molar ratio of carboxylic acid to palladium is held greater than about 10:1 in the process according to the invention. Apart from practical considerations, there is not believed to be an upper limit to this ratio. As explained above, the palladium concentration is preferably as high as possible, which will help determine a practical upper limit. For example, a practical upper limit is about 100:1. Furthermore, the optimum carboxylic acid to palladium ratio depends on the specific carboxylic acid used as co-catalyst. For example, the ratio between mol pentenoic acid per mol palladium is preferably about twice as great as the ratio between mol sterically hindered benzoic acid per mol palladium to achieve favorable results. The carboxylic acid may serve as the solvent of the carbonylation reaction.

The preferred amounts of reactants should preferably be substantially maintained during the entire carbonylation reaction. For example, a continuous carbonylation process is characterized by a residence time, whereas a batch process is characterized by a reaction time. Preferably, the amounts of reactants should be maintained within the preferred ranges for more than about 90%, and more preferably, 95%, of this residence time for a continuous process or reaction time for a batch process.

The temperature of the carbonylation is preferably between about 25° C. and about 200° C., and more preferably, between about 50° C. and about 180° C. The pressure is not particularly critical and generally ranges between about 1 MPa and about 20 MPa, and preferably, is greater than about 2 MPa. An upper limit is not believed to be critical. A very high pressure is disadvantageous because, for example, the process equipment will become very expensive. A practical and preferred upper limit is therefore about 10 MPa. Temperature and pressure conditions may be tailored during scale-up to satisfy specific process needs.

Carbon monoxide can be in a pure form or diluted with an inert gas such as, for example, nitrogen, rare gases or carbon dioxide. In general, more than about 5% hydrogen is undesirable, because this may cause hydrogenation of butadiene under carbonylation conditions. The amount of carbon monoxide is not believed critical if at least a stoichiometric amount of carbon monoxide relative to butadiene is supplied to the carbonylation reaction.

The reaction mixture may optionally contain one or more polymerization inhibitors. Suitable polymerization inhibitors include, for example, quinones, nitro compounds, diphenylamine, tert-butyl catechol and N,N'-naphthyl-p-phenylene diamine.

The carbonylation can be performed batch-wise, semi-continuously or continuously.

In a preferred embodiment, the carbonylation is performed on a continuous or semi-continuous basis. Examples of semi-continuous processes for the preparation of pentenoate ester include a process in which a stirred tank reactor is filled with a catalyst system, a solvent and possibly reactants. Butadiene and optionally the alcohol and/or make up carboxylic acid are continuously supplied. The rate at which butadiene and alcohol are supplied will be determined by the rate at which butadiene reacts and is consumed in the reaction. The rate at which carboxylic acid or small amounts of water, for in situ formation of co-catalyst, has to be supplied will depend on the rate of esterification of the carboxylic acid during carbonylation.

Preferably a continuous process is used. Examples of reactor systems for a continuous process include a series of continuously stirred tank reactors (CSTR) in which a catalyst system, a possible solvent, butadiene, carbon monoxide and alcohol are fed to a first reactor. The various ratios according to the process of the invention can be maintained by controlling the feed rate of the various reactants and catalyst components. The resulting reaction mixture in the first reactor is fed to a second reactor. Fresh butadiene, alcohol and optionally fresh co-catalyst or small amounts of water are fed to the second and further reactors in the appropriate amounts to maintain the desired ratios of the process according to the invention. Instead of a series of CSTR's, a tube reactor can also be used in which, for example, butadiene and alcohol are supplied in intermediate locations along the tube. The catalyst system leaving the last reactor can be separated from the carbonylation products and returned to the first reactor. These reactor systems can also be used when pentenoic acid is the desired product.

Separating the carbon monoxide, butadiene, alcohol and pentenoate ester from the reaction mixture comprising the catalyst system can be performed in various ways. The following description of the separation applies to both cases where pentenoate ester and pentenoic acid are produced. Generally, carbon monoxide can be separated first from the reaction mixture in, for example, a gas-liquid separation unit. The butadiene, alcohol and pentenoate ester can be separated from the reaction mixture containing the catalyst system in one step. This can be followed by isolating the pentenoate ester from butadiene and alcohol. Preferably, the butadiene and alcohol are separated from the reaction mixture in a separate step followed by isolation of the pentenoate ester from the remaining reaction mixture. The various compounds can be separated using a variety of techniques such as, for example, a simple flash operation or by distillation. The choice of unit operation is a function of the physical properties of the compounds to be separated.

The remaining mixture containing the catalyst system comprising the ligand, Pd and the carboxylic acid and, for example, high-boiling by-products and a solvent if present, are returned to the reaction zone to be used in further carbonylation. In order to prevent a build up of, for example, high-boiling by-products in this circulating reaction mixture, a part of this mixture may be purged and reprocessed to retrieve, for example, palladium and/or the phosphine ligand.

Pentenoic acid or pentenoate ester can be, for example, advantageously used as an intermediate compound in the preparation of ε-caprolactam and adipic acid, which are raw materials for the preparation of nylon-6 and nylon-6,6, respectively.

EXAMPLES

The invention is further described by the following non-limiting examples. Conversion (conv.), selectivity (sel.) and activity (act.) are defined as follows:

$$\text{conv. (\%)} = \frac{\text{converted amount of butadiene (mol)}}{\text{initial amount of butadiene (mol)}} \times 100$$

$$\text{sel. of pentenoate (\%)} = \frac{\text{obtained amount of pentenoate (mol)}}{\text{converted amount of butadiene (mol)}} \times 100$$

act. = converted amount of butadiene (mol)/mol Pd/hour.

In these conversion, selectivity and activity calculations, converted amount of butadiene is defined as follows. Butadiene can react to yield at least three possible types of products: (1) the desired pentenoate or pentenoic acid, (2) intermediate products that can react to yield the desired pentenoate or pentenoic acid, and (3) by-products that cannot react to the desired pentenoate or pentenoic acid. These by-products (3) include, for example, butene, vinylcyclohexene and high-boiling products. The high-boiling products include, for example $C_9$ heavy compounds like nonadienoates and the like and higher boiling products.

Converted amount of butadiene means the sum of (1) the amount of the desired pentenoate or pentenoic acid, and (3) the amount of by-products that cannot react to the desired pentenoate or pentenoic acid. Therefore, intermediates products (2) that can react to yield the desired pentenoate or pentenoic acid are not directly included in the calculation of converted amount of butadiene.

Example 1

A 150 ml Parr autoclave made of Hastelloy C was filled successively with 0.47 g (2.1 mmol) of Pd(II) acetate, 5.47 g (20.9 mmol) of triphenyl phosphine, 6.0 g (36.6 mmol) of 2, 4, 6-trimethyl benzoic acid and 35.6 g of diphenyl ether as a solvent. The autoclave was closed and purged three times with 4.0 MPa carbon monoxide. Subsequently, under a pressure of 1.0 Mpa of CO with stirring at a speed of 1250 rpm, a mixture of 2.49 g (78 mmol) of methanol, 3.91 g (73.5 mmol) of butadiene (BD) and 0.70 g of nonane (internal standard for GC product analysis) was injected under pressure from an injection vessel into the autoclave. The temperature of the reaction mixture was raised to 140° C. at a CO pressure of 6.0 MPa. After 10 minutes at this temperature, a continuous butadiene and methanol supply to the reactor was started wherein butadiene and methanol were continuously supplied to the reactor at a constant rate of 142 mmol butadiene and 172 mmol methanol per hour. The butadiene supply was thus 68 mol/mol Pd/hr. After 3.0 hours, the reaction was stopped, and the reaction mixture was analyzed by gas chromatography. The initial start up molar ratio of butadiene/Pd was 35:1. During the operation of this experiment, this ratio increased to 43:1, the ratio at the finish.

The butadiene conversion was 82%. The selectivity to methyl pentenoates (MP) was 93%. The selectivity to trans-methyl-3-pentenoate (t-M3P) was 61.1%, to cis-methyl-3-pentenoate (cis-M3P) was 26.9%, to trans-methyl-2-pentenoate (t-M2P) was 4.7%, to cis-methyl-2-pentenoate (cis-M2P) was 0.2%, and to methyl-4-pentenoate (M4P) was 0.1%. The activity was 60 hr$^{-1}$. 5.4% of the 2,3,6-trimethyl benzoic acid was converted to its methyl ester.

Comparative Example A

A 50 ml Parr autoclave made of Hastelloy C was filled successively with 0.05 g (0.22 mmol) of Pd(II) acetate, 0.61 g (2.32 mmol) of triphenyl phosphine, 0.26 g (1.6 mmol) of 2,4,6-trimethyl benzoic acid and 27.0 g of diphenyl ether as a solvent. The autoclave was closed and purged three times with 4.0 MPa carbon monoxide. Subsequently, under a pressure of 1.0 MPa of CO while stirring at a speed of 1250 rpm, a mixture of 3.76 g (118 mmol) of methanol, 5.14 g (95.3 mmol) of butadiene and 0.45 g of nonane (internal standard for GC product analysis) was injected under pressure from an injection vessel into the autoclave. The temperature of the reaction mixture was raised to 150° C. at a CO pressure of 6.0 MPa. After 5.0 hours, the reaction was stopped, and butadiene and reaction products were analyzed by gas chromatographic methods. The initial butadiene/ palladium ratio was 433:1. During the experiment, this ratio decreased to 61:1.

The conversion was 86%. The selectivity to methyl pentenoates was only 21%, and the activity was only 16 hr$^{-1}$. 9% of the trimethyl benzoic acid was converted to its methyl ester.

Comparative Example B

A 150 ml Parr autoclave made of Hastelloy C was filled successively with 0.182 g (0.81 mmol) of Pd(II) acetate, 2.1 g (8.0 mmol) of triphenyl phosphine, 2.388 g (14.5 mmol) of 2,4,6-trimethyl benzoic acid and 32.4 g of diphenyl ether as a solvent. The autoclave was closed and purged three times with 4.0 MPa carbon monoxide. Subsequently, under a pressure of 1.0 MPa of CO while stirring at a speed of 1250 rpm, a mixture of 1.75 g (32.4 mmol) of butadiene, 1.24 g (38.9 mmol) of methanol and 0.705 g of nonane (internal standard for GC product analysis) was injected under pressure from an injection vessel into the autoclave. The temperature of the reaction mixture was raised to 140° C. at a CO pressure of 6.0 MPa. After 20 minutes at this temperature, butadiene and methanol supplies were started at a constant rate of 105 and 116 mmol per hour respectively, using Gilson model 302 pumps. Thus the butadiene supply was 130 mol/mol Pd/hr. After 5.0 hours, the reaction was stopped, and the butadiene and the reaction products were analyzed by gas chromatographic methods. The initial butadiene/palladium ratio was 49:1. During the experiment, this ratio increased to 220:1.

The conversion was 68%. The selectivity to methyl pentenoates was 64.8%. The selectivity to trans-methyl-3-pentenoate was 43.0%, to cis-methyl-3-pentenoate 19.0%, to trans-methyl-2-pentenoate 2.5%, to cis-methyl-2-pentenoate 0.1%, and to methyl-4-pentenoate 0.1%. The activity was 59 hr$^{-1}$. 8.7% of the trimethyl benzoic acid was converted to its methyl ester.

Comparative Example C

A 50 ml Parr autoclave made of Hastelloy C was filled successively with 0.28 g (1.2 mmol) of Pd(II) acetate, 3.2 g (12.3 mmol) of triphenyl phosphine, 2.1 g (12.6 mmol) of trimethyl benzoic acid and 27.2 g of diphenyl ether as a solvent. The autoclave was closed and purged three times with 4.0 MPa carbon monoxide. Subsequently, under a pressure of 1.0 MPa of CO while stirring at a speed of 1250 rpm, a mixture of 13.6 g (425 mmol) of methanol, 13.8 g (255 mmol) of butadiene and 0.32 g of nonane (internal standard for GC product analysis) was injected under pressure from an injection vessel into the autoclave. The temperature of the reaction mixture was raised to 150° C. at a CO pressure of 9.0 MPa. After 3.0 hours, the reaction was stopped, and the butadiene and the reaction products analyzed by gas chromatographic methods. The initial butadiene/palladium ratio was 213:1. During the experiment, this ratio decreased to 21:1.

The conversion was 90%. The selectivity to methyl pentenoates was 55%, and the activity was 34 hr$^{-1}$. 18% of the trimethyl benzoic acid was converted to its methyl ester.

Examples II–XV

Example I was repeated several times, under different reaction conditions (see Table 1). The temperature was 140° C., unless otherwise stated. Results are listed in Table 1. In all runs, 2,4,6-trimethyl benzoic acid was used as co-catalyst at a molar ratio of 17 versus Pd(II) acetate. Triphenyl phosphine was used as the ligand at a molar ratio of 10 versus Pd(II) acetate. Methanol was supplied at a molar ratio of 1.2 versus the butadiene feed, as in Example I.

TABLE 1

| Ex. num | BD/Pd t = 0 (1) | BD/Pd (2) | BD feed (mol/mol Pd/hr) (3) | Time (hr) | Conv. (%) | Sel MP's (%) | Sel M2P (%) | Act. (hr$^{-1}$) |
|---|---|---|---|---|---|---|---|---|
| II | 44 | 35 | 33 | 4.0 | 84 | 94.2 | 3.0 | 29 |
| III (4) | 43 | 26 | 33 | 6.0 | 89 | 93.5 | 4.2 | 32 |
| IV (5) | 44 | 23 | 35 | 6.0 | 91 | 91.9 | 5.2 | 34 |
| V (6) | 44 | 20 | 32 | 6.0 | 91 | 92.6 | 6.0 | 33 |
| VI (7) | 12 | 8 | 18 | 6.0 | 86 | 92.8 | 7.9 | 20 |
| VII | 23 | 8 | 37 | 6.0 | 94 | 97.4 | 7.6 | 35 |
| VIII | 45 | 32 | 37 | 6.0 | 88 | 92.7 | 4.4 | 35 |
| IX | 44 | 15 | 39 | 4.0 | 93 | 93.6 | 3.7 | 42 |
| X | 44 | 16 | 39 | 4.0 | 92 | 94.4 | 3.8 | 43 |
| XI | 47 | 14 | 36 | 3.1 | 91 | 95.8 | 5.2 | 44 |
| XII | 47 | 18 | 37 | 5.0 | 92 | 94.8 | 6.9 | 40 |
| XIII | 51 | 47 | 53 | 5.0 | 85 | 92.1 | 5.2 | 48 |
| XIV | 29 | 27 | 50 | 4.0 | 88 | 94.7 | 6.2 | 47 |
| XV | 22 | 15 | 40 | 4.5 | 93 | 93.7 | 4.2 | 39 |

(1) initial butadiene/palladium ratio
(2) end of experiment-butadiene/palladium ratio
(3) butadiene feed in mol butadiene per mol Pd per hour
(4) pressure was 5.0 Mpa
(5) pressure was 2.5 Mpa
(6) temperature was 160° C., pressure was 5.5 MPa
(7) pressure was 5.0 MPa Example XVI Example I was repeated, charging the autoclave with 0.453 gram palladium acetate (2.0 mmol), 5.3 gram triphenylphosphine (20 mmol), 9.9 gram benzoic acid (81 mmol), 54.0 gram diphenylether as solvent and 0.976 gram dibenzylether as GC internal standard.

After closing and purging with CO, the reactor was heated to 140° C., under a pressure of 5.5 MPa. When this temperature was reached, a continuous supply of butadiene and methanol was started at rates of 55 and 61 mmol.hr$^{-1}$ respectively. The butadiene supply was thus 28 mol/molPd/hr.

After 6.0 hours, the reaction was stopped, and the mixture analyzed by gas chromatography. At the end of the reaction, the butadiene/Pd ratio was 13. Butadiene conversion was 92%. Selectivity to methylpentenoates was 95.8%. Selectivity to t-M3P was 58.9%, to cis-M3P was 23.4%, to trans methyl-2-pentenoate was 5.3%, to cis-M2P was 0.3% and methyl-4-pentenoate was 0.3%. The activity was 25 mol/molPd/hr. 35% of the benzoic acid was converted to its methyl ester.

Example XVII

Example I was repeated using 3-pentenoic acid as the co-catalyst instead of 2,4,6-trimethyl benzoic acid. 40 molar equivalents pentenoic acid versus Pd(II) acetate were added prior to reaction, and another 20 molar equivalents were added over a period of 5.0 hours during the experiment. Butadiene and methanol were supplied at a rate of 40 and 48 molar equivalents per Pd per hour respectively. The initial and end butadiene/palladium ratios were respectively 20 and 41.

After 5 hours, the conversion was 81%, and the selectivity to methyl pentenoates was 88%. The activity was 29 hr$^{-1}$. 44% of the 3-pentenoic acid (3 PA) was converted to its methyl ester.

Example XVIII

A 150 ml Parr autoclave made of Hastelloy C was filled successively with 0.43 g (1.94 mmol) of Pd(II) acetate, 5.00 g (19.1 mmol) of triphenyl phosphine, 8.54 g (85 mmol) of 3-pentenoic acid, and 0.8 g of nonane (internal standard for GC product analysis) and 55.3 g of diphenyl ether as a solvent. The autoclave was closed and purged three times with 4.0 MPa carbon monoxide. Subsequently the temperature of the reaction mixture was raised to 140° C. at a CO pressure of 4.0 MPa. After heating the reaction mixture to 140° C., and raising the pressure to 4.0 MPa, butadiene was supplied at 83 mmol per hour and methanol at 83 mmol per hour. After one hour, 2.27 g (126 mmol) of water was injected into the autoclave under pressure. The pressure was raised to 6.0 MPa, and butadiene and methanol supply continued at the same rates as during the first hour. After an additional two hours the reaction was stopped, and the contents of the autoclave analyzed by gas-chromatographic methods.

The conversion was 80%. The selectivity to methyl pentenoates was 82%. Only 5% of 3-pentenoic acid was converted to methyl-3-pentenoate.

Example XIX

Example XVII was repeated, except that water was continuously supplied together with methanol at rates of 78 mmol methanol and 54 mmol water per hour. Butadiene was supplied at a rate of 78 mmol per hour. After four hours, the reaction was stopped.

The conversion was 75%, and the selectivity to methyl pentenoates was 79%. No esterification of 3-pentenoic acid was observed.

Example XX

Example I was repeated, using a butadiene feed of 41 mole/mole Pd/hr.

After 4.5 hours of reaction, the reaction mixture was worked-up by distillation at 100° C. and 0.1 mm Hg. The distillation residue was transferred back to the autoclave, and an additional 6 equivalents of 2,4,6-trimethyl benzoic acid relative to palladium and fresh nonane as an internal standard for GC analysis were added. After raising the temperature and pressure to 140° and 6.0 MPa, respectively, the butadiene and methanol feeds were resumed, as in Example 1.

Afterwards, the workup procedure was repeated, and the recycle was then performed another three times. In Table 2, the results of the subsequent cycles are listed.

TABLE 2

| Run # | Conv. | Sel. to MP's | Act. |
|---|---|---|---|
| 1 | 93 | 93.7 | 38 |
| 2 | 97 | 94.3 | 39 |
| 3 | 97 | 95.2 | 39 |
| 4 | 96 | 95.3 | 39 |
| 5 | 97 | 94.6 | 39 |

Comparative Example D

A 150 ml Parr autoclave, made of Hastelloy C, was filled successively with 0.38 g (1.70 mmol) of Pd(II) acetate, 2.87 g (6.7 mmol) of 1,4-bis(diphenylphosphino)-butane, 1.90 g (11.6 mmol) of trimethyl benzoic acid and 32.4 g of diphenyl ether as a solvent. The autoclave was closed and purged three times with 4.0 MPa carbon monoxide. The temperature of the reaction mixture was raised to 140° C. at a CO pressure of 6.0 MPa, and subsequently butadiene and methanol supplies at a constant rate of 160 and 158 mmol per hour respectively were started, using Gilson model 302 pumps. Thus, the butadiene supply was 94 mol/mol Pd/hr. After 2.5 hours, the reaction was stopped, and the butadiene and the reaction products were analyzed by gas chromatographic methods.

The conversion was 80%. The selectivity to methyl pentenoates was 91%. Selectivities were: trans-methyl-3-pentenoate (57%), cis-methyl-3-pentenoate (20%), trans-methyl-2-pentenoate (14%), cis-methyl-2-pentenoate (0%), and methyl-4-pentenoate (0%). The activity was 69 hr$^{-1}$. 20% of the trimethyl benzoic acid was converted to its methyl ester. Therefore, comparative Example D indicates that using a diphosphine ligand yields unfavorable amounts of 2-pentenoate.

Examples XXI–XXVI

A 100 ml Hastelloy C mechanically stirred autoclave was flushed with carbon monoxide. It was then charged via syringe with 75 grams of a mixture of 0.24 grams of palladium acetate (1.07 mmol), 2.92 g of triphenylphosphine (11.1 mmol), a weight of organic acid to supply the mole ratio of acid/Pd shown in Table 3 and the remaining weight as diphenyl ether. The autoclave was sealed and a cold pressure of 0.07 MPa of CO was added. The autoclave was then heated with stirring to 140° C. After reaching temperature the autoclave pressure was immediately adjusted to 3.4 MPa with carbon monoxide. Pumps are used to introduce 4.00 g of butadiene (73.9 mmol) at a pumping rate of 1.80 g/hr. and 2.85 g of methanol (89.1 mmol) at a pumping rate of 1.27 g/hr. The BD/Pd-ratio's in solution were 3.5–21 mole/mole during reaction. The reaction was then allowed to run for a total of 4 hours with intermediate samples taken. The reaction was cooled, vented and the product collected.

A sample of the liquid and gas phase of each product sample was analyzed by capillary gas chromatography. The conversion and selectivity for all major products are shown in Table 3.

TABLE 3

| Acid | Acid/Pd | % BD Conv. | Selectivity to M3P | M2P | C9s |
|---|---|---|---|---|---|
| 3PA | 70 | 95 | 74 | 17 | 3 |
| 2PA | 50 | 70 | 70 | 8 | 9 |
| 3-Butenoic | 50 | 90 | 78 | 8 | 7 |
| Nonanoic | 50 | 89 | 75 | 11 | 8 |
| CHPropionic | 50 | 90 | 78 | 10 | 8 |

2PA = 2-pentenoic acid
CHPropionic = cyclohexylpropionic acid
C9s = nine-carbon dienoic esters (nonadienoic esters)

Example XXVII

A 100 ml Hastelloy C mechanically stirred autoclave was flushed with carbon monoxide. It was then charged via syringe with 80 grams of a mixture of 0.48 grams of palladium acetate (2.14 mmol), 5.84 g of triphenylphosphine (22.3 mmol), 9.72 g of nonanoic acid (56.5 mmol) (to supply the mole ratio of acid/Pd=27) and 64 g of diphenyl ether. The autoclave was sealed and a cold pressure of 0.07 MPa of CO was added. The autoclave was then heated with stirring to 140° C. After reaching temperature, the autoclave pressure was immediately adjusted to 3.4 MPa with carbon monoxide. Pumps are used to introduce 4.00 g of butadiene (73.9 mmol) at a pumping rate of 1.80 g/hr. and 2.40 g of methanol (75.0 mmol) at a pumping rate of 1.27 g/hr. The BD/Pd-ratio in solution was lower than 1 mmol/mol. The reaction was then allowed to run for a total of 4 hours, while taking intermediate samples. The reaction was cooled, vented and the product collected.

A sample of the liquid and gas phase of each product sample was analyzed by capillary gas chromatography. A greater than 99% conversion of butadiene was achieved. The total selectivity to all pentenoic esters and acids was 96%, with 85% to the 3- and 4-isomers. There was also 2% selectivity to nine-carbon dienoic esters, 1.8% to octatrienes and vinylcyclohexene, and 0.2% to saturated six-carbon dimethyl esters.

Example XXVIII

A 100 ml Hastelloy C mechanically stirred autoclave was flushed with carbon monoxide. It was then charged via syringe with 79.4 grams of a mixture of 0.72 grams of palladium acetate (3.21 mmol), 8.76 g of triphenylphosphine (33.4 mmol), 9.78 g of nonanoic acid (56.8 mmol) (to supply the mole ratio of acid/Pd=18) and 60.1 g of diphenyl ether. The autoclave was sealed and a cold pressure of 0.07 MPa of CO was added. The autoclave was then heated with stirring to 140° C. After reaching temperature, the autoclave pressure was immediately adjusted to 3.4 MPa with carbon monoxide. Pumps are used to introduce 4.00 g of butadiene (73.9 mmol) at a pumping rate of 8.1 g/hr. and 2.40 g of methanol (75.0 mmol) at a pumping rate of 5.7 g/hr. The BD/Pd-ratio in solution was 1.4 mole/mole at the end of the reaction. The reaction was then allowed to run for a total of 3 hours with intermediate samples taken. The reaction was cooled, vented and the product collected.

A sample of the liquid and gas phase of each product sample was analyzed by capillary gas chromatography. A 94% conversion of butadiene was achieved. The total selectivity to all pentenoic esters and acids was 95.5%, with 84% to the 3- and 4-isomers. There was also 1.1% selectivity to methylnonadienoates, and 1.6% to methyl 2-methylbutenoate isomers.

While the present invention has been illustrated by means of several preferred embodiments, one of ordinary skill in the art will recognize that changes, modifications, and improvements can be made while still remaining within the scope and spirit of the present invention.

What is claimed is:

1. A process for the preparation of a pentenoic acid or a pentenoate ester by carbonylating butadiene, a butadiene derivative, or a mixture thereof, said process comprising carbonylating said butadiene, butadiene derivative, or mixture thereof, in a reaction mixture in the presence of (i) carbon monoxide, (ii) an alcohol or water, and (iii) a catalyst system comprising palladium, a carboxylic acid, and a monodentate phosphine ligand, wherein in said reaction mixture, the molar ratio of said butadiene, butadiene derivative, or mixture thereof to said palladium is less than about 70:1, the molar ratio of said carboxylic acid to said palladium is greater than about 10:1, and the molar ratio of said alcohol or water to said butadiene, butadiene derivative, or mixture thereof is less than about 2:1, said molar ratios being substantially maintained throughout said carbonylation.

2. A process according to claim 1, wherein said ratio of butadiene, butadiene derivative, or mixture thereof to palladium is greater than about 1:1.

3. A process according to claim 1, wherein said ratio of butadiene, butadiene derivative, or mixture thereof to palladium is less than about 50:1.

4. A process according to claim 1, wherein said ratio of alcohol or water to butadiene, butadiene derivative, or mixture thereof is between about 1:1 and about 1.5:1.

5. A process according to claim 1, wherein said carbonylation is a continuous or semi-continuous carbonylation process step.

6. A process according to claim 5, wherein each of said molar ratios are substantially maintained throughout more than about 90% of said carbonylation.

7. A process according to claim 1, wherein said carboxylic acid is a sterically hindered carboxylic acid having a pKa between about 2 and about 5.0, measured in an aqueous solution at 18° C.

8. A process according to claim 7, wherein said carboxylic acid is a sterically hindered benzoic acid.

9. A process according to claim 1, wherein said carboxylic acid is a pentenoic acid or a nine-carbon carboxylic acid.

10. A process according to claim 1, wherein said carbonylation is performed continuously, and any esterification product of said carboxylic acid formed during said carbonylation is hydrolyzed back to said carboxylic acid in a separate step and reused in said continuously performed carbonylation.

11. A process according to claim 1, wherein said alcohol is methanol or ethanol.

12. A process according to claim 1, wherein said alcohol is a $C_1$–$C_{20}$ alcohol with one or more hydroxy groups.

13. A process according to claim 1, wherein said monodentate phosphine ligand is represented by the formula:

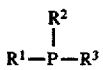

wherein $R^1$, $R^2$ and $R^3$ each individually represent an optionally substituted organic group.

14. A process for the preparation of a pentenoic acid or a pentenoate ester by carbonylating butadiene, a butadiene derivative, or a mixture thereof, said process comprising carbonylating said butadiene, butadiene derivative, or mixture thereof in a reaction mixture in the presence of (i) carbon monoxide, (ii) methanol, ethanol, or a mixture thereof, and (iii) a catalyst system comprising palladium, a sterically hindered carboxylic acid with a pKa of less than 4.5, and a monodentate phosphine ligand, wherein in said reaction mixture, the molar ratio of said butadiene, butadiene derivative, or mixture thereof to said palladium is less than about 70:1, the molar ratio of said carboxylic acid to said palladium is greater than about 10:1, and the molar ratio of said methanol or ethanol to said butadiene, butadiene derivative, or mixture thereof is less than about 2:1, said molar ratios being substantially maintained throughout said carbonylation.

15. A process according to claim 14, wherein said monodentate phosphine ligand is a triphenyl phosphine ligand.

16. A process according to claim 14, wherein said carbonylation is continuous and said molar ratios are maintained throughout more than about 90% of said carbonylation.

* * * * *